(12) United States Patent
Koura et al.

(10) Patent No.: US 6,429,173 B1
(45) Date of Patent: Aug. 6, 2002

(54) DEFLORATION AGENT FOR APPLE TREES

(75) Inventors: Seigo Koura, Miyazaki-Ken; Takashi Nakayama, Tokyo; Kiyoshi Yokota, Morioka, all of (JP)

(73) Assignee: Agro-Kanesho Co., Ltd., Tokyo (JP)

( * ) Notice: Subject to any disclaimer, the term of this patent is extended or adjusted under 35 U.S.C. 154(b) by 0 days.

(21) Appl. No.: 09/721,648

(22) Filed: Nov. 27, 2000

Related U.S. Application Data

(63) Continuation of application No. PCT/JP98/02290, filed on May 26, 1998.

(51) Int. Cl.[7] .................. A01N 37/10; A01N 57/02
(52) U.S. Cl. ................................................ 504/127
(58) Field of Search ........................................ 504/127

(56) References Cited

U.S. PATENT DOCUMENTS 3,879,188 A    4/1975  Fritz et al. .................. 71/86

5,242,891 A  *  9/1993  Larsen et al. ................ 504/127

FOREIGN PATENT DOCUMENTS

| JP | 3-173807 | 7/1991 |
| JP | 6-92804 | 4/1994 |
| JP | 6-100407 | 4/1994 |
| JP | 7-118108 | 5/1995 |
| JP | WO99/60854 | 12/1999 |

* cited by examiner

Primary Examiner—S. Mark Clardy
(74) Attorney, Agent, or Firm—Oblon, Spivak, McClelland, Maier & Neustadt, P.C.

(57) ABSTRACT

The present invention relates to a defloration agent for apple trees. The present defloration agent comprises 3-(2-methyl-4-chlorophenoxy)butyric acid (MCPB) or an ester thereof and 2-chloroethylphosphonic acid (ethephon). The present invention provides an excellent defloration effect even when the temperature is low in the blossoming season.

34 Claims, No Drawings

DEFLORATION AGENT FOR APPLE TREES

This application is a continuation of international application Ser. No. PCT/JP98/02290, filed May 26, 1998.

BACKGROUND OF THE INVENTION

1. Field of the Invention

The present invention relates to a defloration agent for apple trees. In particular, the present invention relates to a defloration agent for apple trees, comprising 3-(2-methyl-4-chlorophenoxy)butyric acid or an ester thereof and ethephon as active ingredients.

2. Description of the Background

When flowers are left as they are after blooming and pollination, most of them bear fruits. The fruits are, therefore, small and the quality of them is low and, in addition, such a large number of fruits is too heavy a burden for the tree. To solve these problems, fruit thinning was usually conducted by human hands. Recently, chemical substances began to be used as defloration agents or fruit thinners. In particular, defloration agents used in an initial stage of blooming are important because they inhibit the growing of superfluous fruits.

Lime/sulfur mixture, calcium alkylbenzenesulfonates, etc. are now being used as defloration agents. However, lime/sulfur mixture has defects in that the effect thereof is unstable, in that it has a phytotoxic effect on leaves and further in that it is often harmful to honeybees. The calcium alkylbenzenesulfonates also have defects in that they must be applied 3 or 4 times during the flowering period, in that a lot of manpower is necessitated and in that they do not work instantly. As for effective means of solving these problems, JP Kokai No. 7-118108 discloses a technique of using 3-(2-methyl-4-chlorophenoxy)butyric acid or an ester thereof (2-methyl-4-chlorobutyric acid compounds).

However, the technique of JP Kokai No. 7-118108 has a problem in that its effect is not always perfect when the temperature is extremely low in the blossoming season, while it is effective when the weather is settled.

SUMMARY OF THE INVENTION

Therefore, the object of the present invention is to provide a defloration agent which exhibits an excellent defloration effect even when the temperature is low in the blossoming season.

DETAILED DESCRIPTION OF THE PREFERRED EMBODIMENTS

After intensive investigations made for the purpose of attaining the above-described object, the inventors have found that a defloration agent which exhibits an excellent defloration effect even under a low temperature condition can be obtained by using 3-(2-methyl-4-chlorophenoxy) butyric acid in combination with 2-chloroethylphosphonic acid (ethephon). Thus, the present invention relates to a defloration agent characterized by containing 3-(2-methyl-4-chlorophenoxy)butyric acid together with ethephon.

The detailed description will be made on the present invention.

The defloration agent of the present invention is suitable for use for apple trees. This defloration agent is usable for various kinds of apple trees. In them, Fuji apple tree is preferred.

3-(2-Methyl-4-chlorophenoxy)butyric acid or esters thereof usable in the present invention have a structure represented by following formula (I):

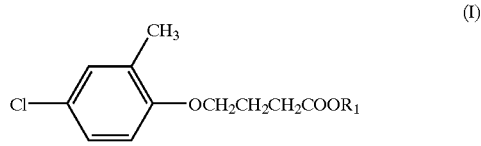

wherein $R_1$ represents a hydrogen atom, a methyl group, an ethyl group or a propyl group.

This compound is already known and disclosed in JP Kokai No. 7-118108 as described above.

Compound (I) is incorporated in the defloration agent in an amount of usually 0.1 to 90% by weight, preferably 0.5 to 50% by weight, and more preferably 1 to 30% by weight, based on the defloration agent.

The concept of "defloration agent" herein includes a preparation, the compound itself or a spray including a diluted preparation.

Ethephon used in the present invention is 2-chloroethylphosphonic acid. This compound itself is also well known. However, it has not been specially reported that ethephon is a compound useful as the defloration agent. Ethephon is suitably incorporated in the defloration agent in an amount of usually 0.1 to 90% by weight, preferably 0.5 to 50% by weight, and more preferably 5 to 40% by weight, based on the defloration agent.

The weight ratio of compound (I) to ethephon is usually 1/1 to 1/50, preferably 1/2 to 1/10.

The defloration agent of the present invention can be usually mixed with a solid carrier, a solvent, a surfactant (including a spreader, an emulsifier or the like) and other adjuvants for preparations (such as an antifreezing agent, an antiseptic and an inorganic salt) to obtain an emulsion, aqueous solution, wettable powder, microemulsion, suspension, wettable granules, solid emulsion, water-soluble powder or the like.

When the decoration agent is applied to apple trees, compound (I) is diluted to a concentration of usually 1 to 100 ppm, preferably 10 to 50 ppm. On the other hand, ethephon is diluted to a concentration of usually 10 to 500 ppm, preferably 30 to 200 ppm.

The solid carriers are preferably those in the form of a fine powder or granules. They include, for example, fine inorganic mineral powders such as synthetic silicic acid, clay, kaolin, talc, radiolite, acid clay, pyrophyllite, bentonite, diatomaceous earth and clay minerals; vegetable powders such as soybean powder, walnut shell powder, starch, powdered milk and saccharides; fine powders of polymers such as petroleum resin, PVA, CMC and polyacrylates; urea; and waxes.

The solvents include, for example, aromatic and aliphatic hydrocarbons such as xylene, naphthas, methylnaphthalene, paraffins and machine oils; alcohols such as isopropanol, butanol, propylene glycol, ethylene glycol, cellosolves and carbitol; ketones such as acetone, cyclohexanone and isophorone; vegetable oils such as soybean oil and cotton seed oil; dimethyl sulfoxide, N,N-dimethylformamide, N-methylpyrrolidone, acetonitrile and water.

The surfactants used for the emulsification, dispersion, wetting, etc. are not particularly limited, and they include, for example, nonionic surfactants, anionic surfactants, cationic surfactants and amphoteric surfactants. The nonionic surfactants are, for example, polyoxyethylene alkyl ethers, polyoxyethylene alkylaryl ethers, polyoxyethylene fatty acid esters, polyoxyethylene/polyoxypropylene block copolymer, sorbitan fatty acid esters, polyoxyethylene sorbitan fatty acid esters, polyoxyethylene styrenated and benzylated phenyl ethers. The anionic surfactants are, for example, lignin sulfonic acid salts, alkylnaphthalenesulfonic acid salts, naphthalenesulfonic acid salt/formaldehyde condensates, alkylsulfuric acid ester salts, alkylsulfonic acid salts, alkylarylsulfonic acid salts, dialkylsulfosuccinic acid salts, polyoxyethylene alkylaryl ether sulfates, sulfonates or phosphates, polyoxyethylene alkyl ether sulfates, phosphates or sulfonates, and polyoxyethylene/styrenated and benzylated phenyl ether phosphoric or sulfuric acid ester salts.

Other adjuvants include, for example, alginic acid salts, polyvinyl alcohol (PVA), gum arabic, carboxymethylcellulose (CMC), xantham gum, welan gum and acid isopropyl phosphate.

Since Compound (I) used in the present invention is in a liquid form and insoluble in water, the defloration agent containing this compound is practically usable in various formulations such as wettable powder, emulsion, microemulsion, aqueous solution, water-soluble powder, wettable granules and solid emulsion. Of course, the formulations are not necessarily limited to them.

The above-described formulations can be easily produced by ordinary techniques by those skilled in the art. The brief description will be made on typical formulations. The defloration agent of the present invention may contain both Compound (I) and ethephon in the same preparation, or preparations each containing Compound (I) or ethephon may be mixed together to form the intended preparation. Further, both preparations each containing Compound (I) or ethephon may be mixed in an aqueous diluent. In such a case, methods for producing the preparation containing Compound (I) and also for producing the preparation containing ethephon can be the same.

The stable emulsion and aqueous solution can be obtained by mixing the active ingredients with a surfactant such as an emulsifier or a spreader, an aromatic or mineral oil solvent, and optional ingredients such as cyclohexanone, N-methyl-2-pyrrolidinone, methylnaphthalene, alkyl phthalates, alkylbenzenes, lower alcohols, ketone, glycol, glycerol, cellosolves, carbitol, polyalkylene glycols, dibasic acid esters, aliphatic acid esters and vegetable oils and then diluting the mixture in water.

The wettable powder can be obtained by mixing the active ingredients with the above-described emulsifier and solvent, then adsorbing the obtained mixture on (or mixing the mixture with) a fine powder of an inorganic mineral such as synthetic silicic acid, clay, kaolin, talc, radiolite, bentonite, diatomaceous earth or clay minerals or a vegetable powder such as soybean powder, starch, powdered milk or a saccharide, a fine powder of a polymer such as PVA, CMC or a polyacrylate, a water-soluble inorganic salt such as a sulfate, phosphate or nitrate or potassium chloride, or urea, pulverizing the obtained product and mixing it with an anionic or nonionic surfactant to impart wettability or suspending property to the obtained mixture.

The microemulsion can be obtained by solubilizing the active ingredients in water with a surfactant having a high solubilizing effect, usually a nonionic surfactant or anionic surfactant having a strong solubilizing effect, to form an aqueous microemulsion of fine particles, and then adding an antifreezing agent and an antiseptic such as a lower alcohol, glycol or glycerol thereto.

The thick emulsion can be obtained by emulsifying the active ingredients with an emulsifying machine or a high-speed stirrer in the presence of a surfactant or a water-soluble polymer, and then adding a water-soluble polymer compound having a thixotropic property, a high-molecular weight surfactant having a protective colloidal property, antifreezing agent, antiseptic, etc. to further improve the stability.

The effect of the defloration agent of the present invention can be obtained by applying the defloration agent in a period between the initial stage of blossoming of the central flower and the final stage of blossoming of the lateral flowers, namely, in the entire course of the blossoming. A particularly high effect can be obtained when the defloration agent is applied in a period ranging from immediately after the full blossom to two days thereafter. The defloration effect of this agent is exhibited particularly on the lateral flowers and is substantially ineffective on the central flowers. This is an excellent characteristic of the defloration agent of the present invention.

The defloration agent of the present invention may be used in the form of a formulation having a previously controlled concentration or in the form of a diluted spray having the above-described application concentration.

In the practical use of the defloration agent of the present invention, a suitable selection or combination of the formulation type, dilution rate (concentration), amount of the agent to be applied, spraying machine or method, and additives is necessary depending on the intended defloration rate, kind of apple bearing trees, age of the trees, tree vigour, control of fertilizer and water, application time, weather conditions, etc.

The term "low temperature" herein indicates a temperature lower than the average temperature by, for example, 2 to 10° C., particularly 2 to 7° C. Concretely, the average temperature in the blossoming period of apple trees is usually higher than 17° C. in Aomori Prefecture which is famous for producing apples in Japan. When bad weather lasts for a long time, the average temperature in the flowering season is below 15° C. in some cases.

Examples

The following Examples will further illustrate the present invention, which by no means limit the scope of the invention. In the Examples, percentages are given by weight.

[Compounds Used]

Compounds (I)

Compound A [3-(2-methyl-4-chlorophenoxy)butyric acid]

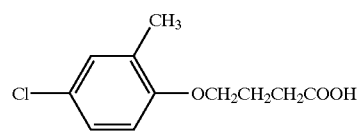

(melting point: 100° C.)

Compound B [ethyl 3-(2-methyl-4-chlorophenoxy) butyrate]

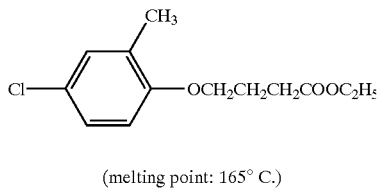

(melting point: 165° C.)

Ethephon (RT)

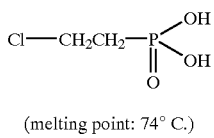

(melting point: 74° C.)

[Formulation]
Production of Microemulsion (ME) Preparation of Compound (I)

3% ME preparation was produced by mixing polyoxyethylene tristyrylphenyl ether with calcium dodecylbenzene sulfonate.

The dilution rate was 1/1500 (20 ppm) or 1/2000 (15 ppm).

Production of Ethephon Preparation

10% aqueous solution of ethephon was produced by mixing 15 parts (by weight) of ethephon (purity: 70%) with 85 parts of water.

The dilution rate was 1/1000 (100 ppm) or 1/2000 (50 ppm).

[Biological Assay]

The ME preparation and ethephon preparation produced as described above were mixed together to obtain an application solution. The concentrations of Compound (I) and ethephon in the spray were as shown in Tables 1 and 2.

A branch having about 50 bunches of flowers was selected from a 13-year old apple tree (variety: Fuji). The application solution produced as described above was sprayed over the whole branch with a knapsack sprayer on the day after the full blossom of the central flower. 30 days after the spraying, the defloration effect was examined to obtain the results shown in Table 1. The effect obtained at a low temperature is shown in Table 2. The evaluation results are shown by percentages of remaining fruits (both central and lateral fruits) calculated by the formula shown below. The phytotoxicity was determined on the basis of defoliation, discolored leaves, state of leaves and also state of russet, and the results were classified into the following 5 ranks (− to +++).

Percentage of remaining fruits ≈ number of normal fruits on the test day/number of flowers on the treatment day × 100

Standard of Determination of Phytotoxicity
−: none
±: Phytotoxicity was extremely slight.
+: Phytotoxicity was only slight.
++: Phytotoxicity was not so serious.
+++: Phytotoxicity was serious.

TABLE 1

Ordinary temperature condition
(average temperature in flowering period: 17.5° C.)

| Ingredient concentration (ppm) | | Fruit setting rate (%) | | |
|---|---|---|---|---|
| Ethephon | | Lateral fruit | Central fruit | Phytotoxicity to leaves and fruits |
| Compound A | | | | |
| 20 | 0 | 19 | 76 | — |
| 15 | 0 | 27 | 81 | — |
| 15 | 50 | 14 | 70 | — |
| Compound B | | | | |
| 20 | 0 | 13 | 75 | — |
| 15 | 0 | 28 | 80 | — |
| 15 | 50 | 11 | 74 | — |
| 1/100 Lime sulfur application (once) (comparison) | | 43 | 69 | + browning |
| Untreated | | 70 | 85 | — |

TABLE 2

Low temperature condition
(average temperature in flowering period: 14.6° C.)

| Ingredient concentration (ppm) | | Fruit setting rate (%) | | |
|---|---|---|---|---|
| Ethephon | | Lateral fruit | Central fruit | Phytotoxicity to leaves and fruits |
| Compound A | | | | |
| 20 | 0 | 39 | 78 | — |
| 15 | 0 | 43 | 81 | — |
| Compound B | | | | |
| 20 | 0 | 36 | 79 | — |
| 15 | 0 | 40 | 76 | — |
| Compound A | | | | |
| 15 | 50 | 28 | 67 | — |
| 15 | 100 | 20 | 63 | — |
| Compound B | | | | |
| 15 | 50 | 26 | 65 | — |
| 15 | 100 | 19 | 59 | — |
| 0 | 100 | 42 | 83 | — |
| 1/100 Lime sulfur application (once) (comparison) | | 50 | 77 | + browning |
| Untreated | | 53 | 82 | — |

It is apparent from the above experiments that the defloration agent of the present invention for apple trees has the following effects: the reduction in the rate of remaining lateral flowers in the apical buds and the lateral buds was remarkable as compared with the untreated case. The defloration agent of the present invention was substantially not effective on pollinated central flowers. The effect of this agent is more remarkable than that of 1/100 dilution (practical concentration) of lime sulfur (liquid concentrate: 11%) available on the market. When compound (I) was used alone, a high defloration effect can be obtained even at a low temperature at which a sufficient defloration effect cannot be obtained in general. In addition, the phytotoxicity causing the browning of leaves or malformed leaves as observed when lime sulfur is applied is not observed. This fact shows an extremely high safety. The defloration agent of the present invention exhibits its defloration effect in such a manner that the lateral flowers are dropped before the seed-setting to keep only the central flowers to grow normally. Such a defloration effect is a new effect which cannot be obtained in the prior art. This is a great characteristic feature of the defloration agent of the present invention. Thus, the defloration agent of the present invention fully satisfies requirements in the prior art. The remarkable effect of the defloration agent is expected even at a low temperature. The usefulness of the defloration agent is great.

What is claimed is:

1. A defloration composition, comprising:
   a) 3-(2-methyl-4-chlorophenoxy)butyric acid or an ester thereof having the formula:

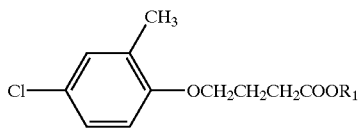

wherein $R_1$ represents hydrogen, methyl, ethyl or propyl; and
   b) 2-chloroethylphosphonic acid (ethephon).

2. The defloration composition of claim 1, wherein $R_1$ is hydrogen.

3. The defloration composition of claim 1, wherein $R_1$ is methyl.

4. The defloration composition of claim 1, wherein $R_1$ is ethyl.

5. The defloration composition of claim 1, wherein $R_1$ is propyl.

6. The defloration composition of claim 1, wherein said 3-(2-methyl-4-chlorophenoxy)butyric acid or an ester thereof is contained in an amount of 0.1 to 90% by weight.

7. The defloration composition of claim 6, wherein said 3-(2-methyl-4-chlorophenyl)butynic acid or an ester thereof is contained in an amount of 0.5 to 50% by weight.

8. The defloration composition of claim 7, wherein said 3-(2-methyl-4-chlorophenyl)butyric acid or an ester thereof is contained in an amount of 1 to 30% by weight.

9. The defloration composition of claim 1, wherein said ethephon is contained in an amount of 0.1 to 90% by weight.

10. The defloration composition of claim 9, wherein said ethephon is contained in an amount of 0.5 to 50% by weight.

11. The defloration composition of claim 1, which further comprises a carrier.

12. The defloration composition of claim 11, which is a form of an emulsion.

13. The defloration composition of claim 11, which is in a form of an aqueous solution.

14. The defloration composition of claim 11, which is in a form of a wettable powder.

15. The defloration composition of claim 11, which is in a form of a microemulsion.

16. The defloration composition of claim 11, which is in a form of a suspension.

17. The defloration composition of claim 11, which is in a form of wettable granules.

18. The defloration composition of claim 11, which is in a form of a solid emulsion.

19. The defloration composition of claim 11, which is in a form of a water-soluble powder.

20. The defloration composition of claim 11, wherein said compound (a) is present in an amount of from 1 to 100 ppm.

21. The defloration composition of claim 20, wherein said compound (a) is present in an amount of from 10 to 50 ppm.

22. The defloration composition of claim 11, wherein said compound (b) is present in an amount of from 10 to 500 ppm.

23. The defloration composition of claim 22, wherein said compound (b) is present in an amount of from 30 to 200 ppm.

24. The defloration composition of claim 21, which further comprises a surfactant.

25. The defloration composition of claim 11, which further comprises an antifreeze compound.

26. A method of deflowering apple trees, which comprises applying an effective amount of the defloration composition of claim 1, to flowers of an apple tree.

27. The method of claim 26, wherein the apple tree is the variety Fuji.

28. The method of claim 26, wherein said composition is applied to the flowers of apple trees in a period ranging from the initial stage of blossoming of the central flowers to the final stage of blossoming of the lateral flowers.

29. The method of claim 26, wherein said 3-(2-methyl-4-chlorophenoxy)butyric acid or ester thereof is contained in the composition in an amount of from 0.1–90% by weight.

30. The method of claim 26, wherein said component b) is contained in the composition in an amount of from 0.1–90% by weight.

31. The method of claim 26, wherein said applied composition is in a form of an emulsion, an aqueous solution, a wettable powder, a microemulsion, suspension, wettable granules, solid emulsion or water-soluble powder.

32. The method of claim 26, wherein said applied composition is in a form of a microemulsion.

33. The method of claim 26, wherein said 3-(2-methyl-4-chlorophenoxy)butyric acid or ester thereof is applied at a concentration of 1–100 ppm.

34. The method of claim 26, wherein said ethephon is applied at a concentration of 10–500 ppm.

* * * * *